United States Patent
Yamamoto et al.

(10) Patent No.: US 11,414,340 B2
(45) Date of Patent: *Aug. 16, 2022

(54) HIGH STRENGTH LITHIUM SILICATE GLASS CERAMIC HAVING HIGH SHIELDING PROPERTY

(71) Applicant: SHOFU INC., Kyoto (JP)

(72) Inventors: Kazuki Yamamoto, Kyoto (JP); Daisuke Takeuchi, Kyoto (JP)

(73) Assignee: SHOFU INC., Kyoto (JP)

(*) Notice: Subject to any disclaimer, the term of this patent is extended or adjusted under 35 U.S.C. 154(b) by 0 days.

This patent is subject to a terminal disclaimer.

(21) Appl. No.: 16/148,033

(22) Filed: Oct. 1, 2018

(65) Prior Publication Data
US 2019/0202731 A1    Jul. 4, 2019

(30) Foreign Application Priority Data
Oct. 2, 2017    (JP) .............................. JP2017-192531

(51) Int. Cl.
| C03C 10/04 | (2006.01) |
| C03C 10/02 | (2006.01) |
| C03C 10/00 | (2006.01) |
| C03C 3/095 | (2006.01) |
| C03C 4/00  | (2006.01) |

(Continued)

(52) U.S. Cl.
CPC .......... *C03C 10/0009* (2013.01); *C03C 3/095* (2013.01); *C03C 3/097* (2013.01); *C03C 4/0021* (2013.01); *C03C 10/0054* (2013.01); *A61K 6/833* (2020.01); *C03C 2203/52* (2013.01); *C03C 2204/00* (2013.01)

(58) Field of Classification Search
CPC ..... C03C 10/00; C03C 10/0009; A61K 6/833; A61K 6/836
See application file for complete search history.

(56) References Cited

U.S. PATENT DOCUMENTS 3,811,853 A * 5/1974 Bartholomew ....... C03C 4/0064
                                                          65/23
9,125,812 B2 * 9/2015 Durschang ............. A61C 8/005
(Continued)

FOREIGN PATENT DOCUMENTS

| CN | 103945819 | 7/2014 |
| EP | 3 225 227 | 10/2017 |

(Continued)

OTHER PUBLICATIONS

Extended European Search Report dated May 7, 2019 in corresponding European Patent Application No. 18198111.9.
(Continued)

*Primary Examiner* — Karl E Group
(74) *Attorney, Agent, or Firm* — Wenderoth, Lind & Ponack, L.L.P.

(57) ABSTRACT

To provide An $Al_2O_3$-free dental lithium silicate glass composition comprising the following components:
$SiO_2$: 60.0 to 80.0% by weight
$Li_2O$: 10.0 to 17.0% by weight
$K_2O$: 0.5 to 10.0% by weight
a nucleating agent: 1.0 to 6.0% by weight
a colorant: 0.0 to 10.0% by weight, and,
a metal oxide Me(tetravalent)$O_2$: 5.0 to 10.0% by weight.

4 Claims, 3 Drawing Sheets

(51) Int. Cl.
*C03C 3/097* (2006.01)
*A61K 6/833* (2020.01)

(56) References Cited

U.S. PATENT DOCUMENTS

| | | |
|---|---|---|
| 9,206,077 B2* | 12/2015 | Durschang .............. C03B 32/02 |
| 9,260,342 B2 | 2/2016 | Borczuch-Laczka et al. |
| 9,730,863 B2* | 8/2017 | Durschang .............. A61K 6/82 |
| 10,391,039 B2* | 8/2019 | Takeuchi ................. A61C 5/77 |
| 2013/0295523 A1 | 11/2013 | Durschang et al. |
| 2014/0223965 A1 | 8/2014 | Ritzberger et al. |
| 2014/0252272 A1 | 9/2014 | Durschang et al. |
| 2015/0140274 A1 | 5/2015 | Bürke et al. |
| 2016/0060159 A1 | 3/2016 | Kim et al. |
| 2016/0236971 A1 | 8/2016 | Rampf et al. |
| 2018/0009701 A1 | 1/2018 | Rampf et al. |
| 2019/0047905 A1* | 2/2019 | Dittmer ................... C03C 3/097 |
| 2019/0177210 A1* | 6/2019 | Beall ......................... C03C 4/16 |
| 2019/0256407 A1* | 8/2019 | Beall ....................... A61K 6/824 |

FOREIGN PATENT DOCUMENTS

| | | |
|---|---|---|
| JP | 2013-543831 | 12/2013 |
| JP | 2015-517337 | 6/2015 |
| JP | 2017-501098 | 1/2017 |
| WO | 2016/120146 | 8/2016 |

OTHER PUBLICATIONS

Office Action dated Feb. 22, 2022, in corresponding Chinese Patent Application No. 201811169879.7, with English translation.
Notification of Reasons for Refusal dated May 16, 2022, in corresponding Japanese Patent Application No. 2018-187009, with English translation.

* cited by examiner

[Fig. 1]
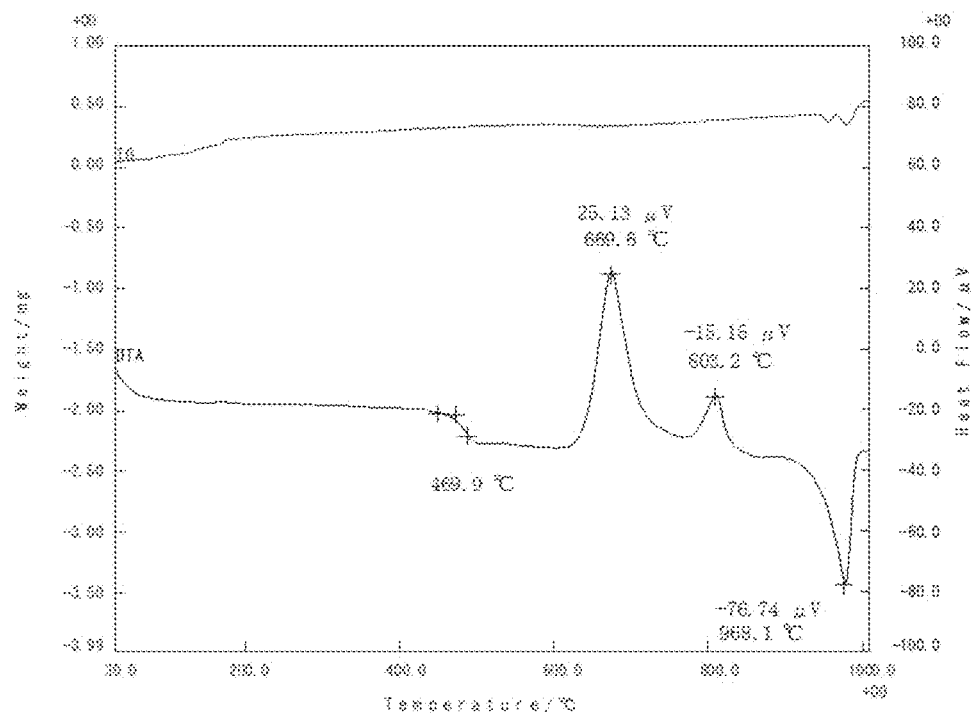
[Fig. 2]
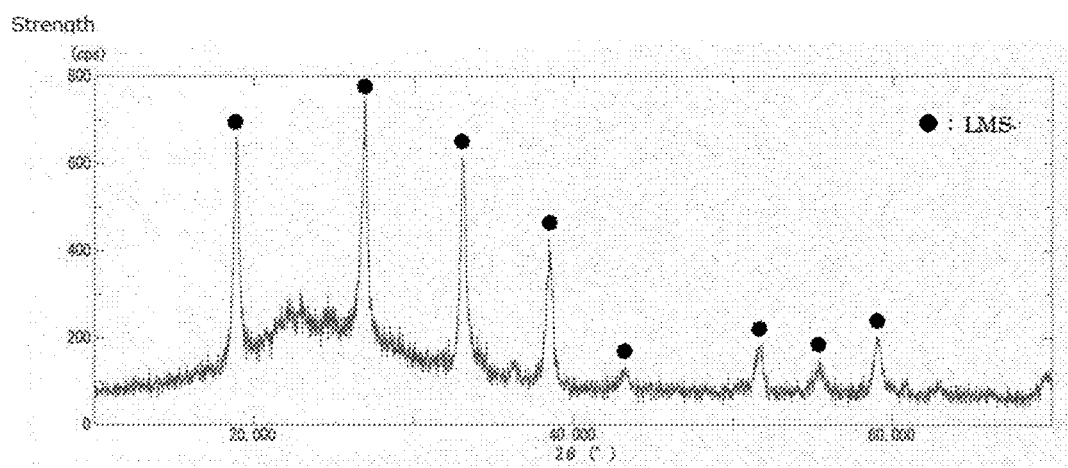

[Fig. 3]
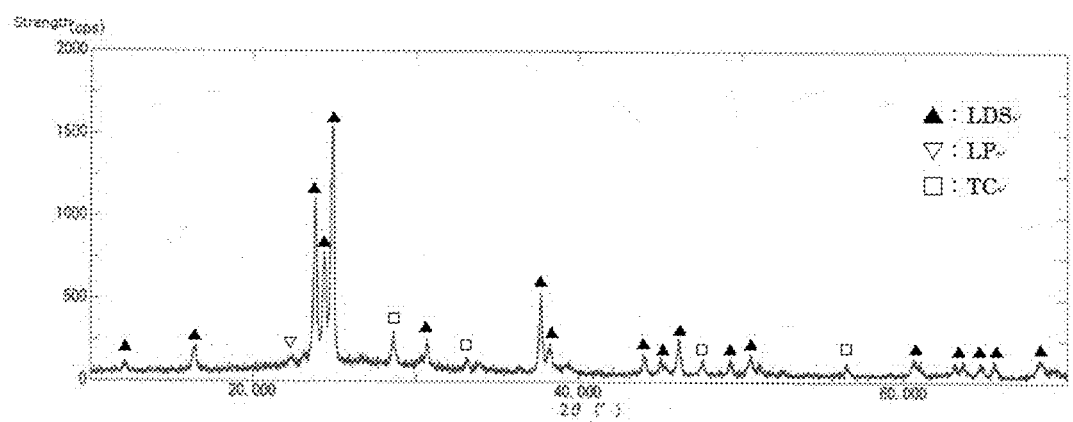
[Fig. 4]
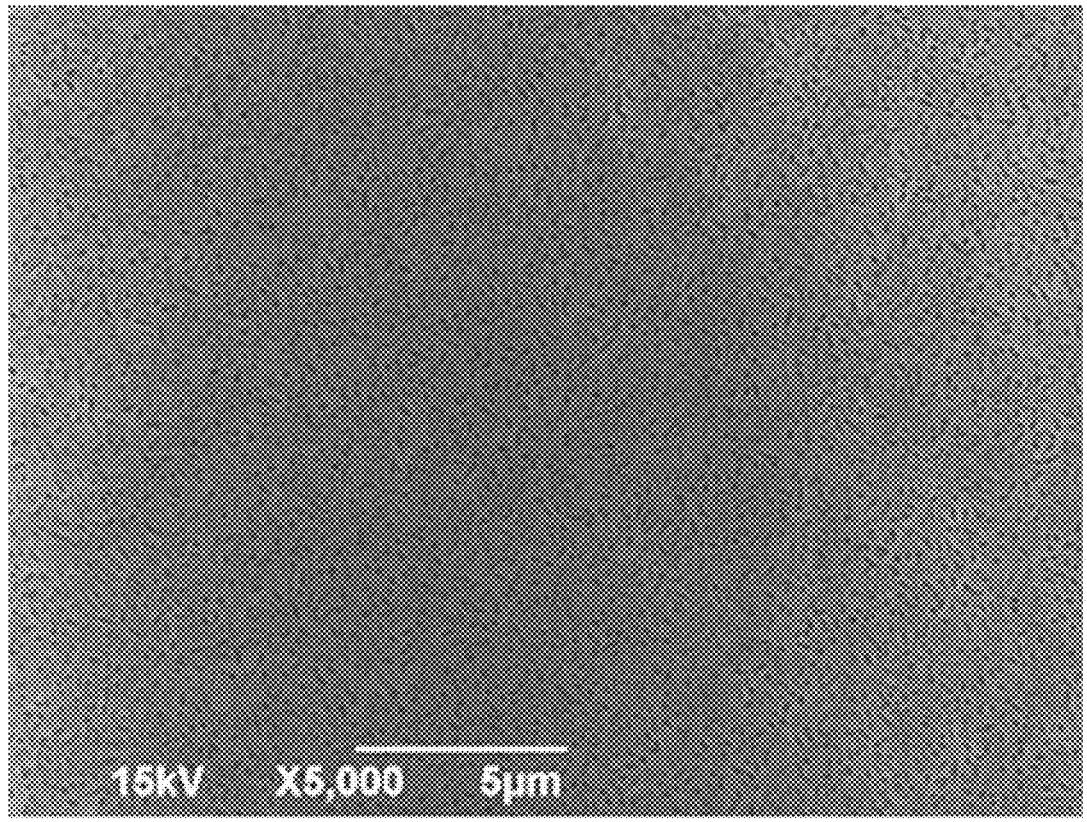

[Fig. 5]
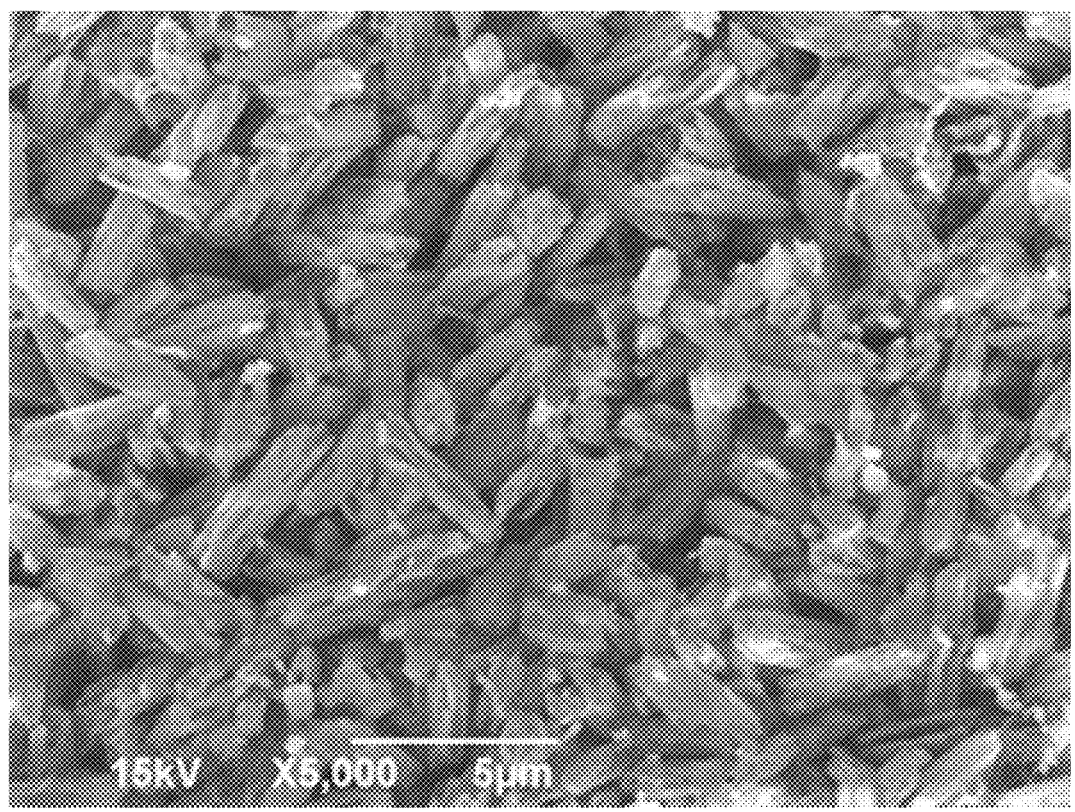

HIGH STRENGTH LITHIUM SILICATE GLASS CERAMIC HAVING HIGH SHIELDING PROPERTY

CROSS-REFERENCE TO RELATED APPLICATIONS

This application is based on and claims the benefit of priority from Japanese Patent Application Serial No. 2017-192531 (filed on Oct. 2, 2017), the contents of which are hereby incorporated by reference in their entirety.

BACKGROUND OF THE INVENTION

Field of the Invention

The present invention relates to a lithium silicate glass composition used in the preparation of a ceramic dental crown restorative material used for the aesthetic restorative treatment in the dental field, a glass ceramic obtained by heat treating the lithium silicate glass composition, and a dental crown restorative material prepared by using the heat treated glass ceramic. More specifically, the present invention relates to a lithium silicate glass composition in which lithium disilicate and/or lithium metasilicate are precipitated as a main crystal phase and a single crystal and/or a composite crystal of a tetravalent metal oxide are precipitated as a secondary crystal phase, a glass ceramic obtained from the lithium silicate glass composition, and a dental crown restorative material prepared by using the glass ceramic.

Description of the Related Art

In the aesthetic restorative treatment in the dental field, dental crown restorative materials made of ceramics have hitherto been used clinically; however, most of such materials have been glass ceramics including leucite crystal (KAlSi$_2$O$_6$). The refractive index of the leucite crystal approximates to the refractive index of the surrounding glass matrix, accordingly the glass ceramics including the crystal have transparency, and consequently aesthetically excellent dental crown restorative materials have been able to be prepared. However, leucite crystal is dendrites, accordingly cannot suppress the development of cracks generated in the interiors of the glass ceramics, and hence the materials including leucite crystal have been unable to obtain high material strength.

Thus, recently, as glass ceramics to develop high strength, lithium silicate glass ceramics have been applied clinically. The lithium silicate glass is material in which by heat treating, characteristic forms of crystals (lithium disilicate and/or lithium metasilicate) are precipitated in high densities; and the lithium silicate glass ceramic has a structure in which these crystals are mutually entangled, and accordingly suppress the development of cracks and develop high material strength. At present, the use of these lithium silicate glass has been expanded to various applications in the dental field; examples of such a use include powdery porcelain materials for building up/burning and ceramic blanks for press molding or CAD/CAM mechanical processing.

In addition, the lithium silicate glass ceramic has a feature in aesthetic property approximating to natural teeth as well as the strength. The tooth restorative materials corresponding various portions can be prepared by adjusting the transparency. In addition, it is possible to provide a dental crown restorative material having high compatibility and adhesive property to an upper layer porcelain which is a leucite based grass ceramics and a high aesthetic property. In recent year, there are many reports of the prior art with respect to the lithium silicate glass ceramics.

U.S. Pat. No. 9,260,342 B2 discloses that first crystal (lithium disilicate) and second crystal (crystal chosen from the group consisting of lithium aluminosilicates: LiAlSi$_2$O$_6$, LiAlSi$_3$O$_8$, LiAlSi$_4$O$_{10}$) are precipitated by heat treating a lithium silicate glass composition in which 10.1 wt. % or more of Al$_2$O$_3$ and 10.1 wt. % or more of Li$_2$O are contained and the content ration of the Al$_2$O$_3$ and Li$_2$O is within a range of 1:1 to 1.5:1, to exhibited high material strength. In addition, in this prior art document, a gradation exhibited by using optical properties of two kinds of crystals (lithium disilicate crystal phase: translucent, lithium aluminosilicate: opaque) is described as one future.

US20160060159A1 discloses that the compression stress is increased by precipitating of a cristobalite crystal in addition to a lithium disilicate crystal to increase the strength. However, when the cristobalite crystal is excessively formed, a difference of the coefficient of thermal expansion becomes large, therefore microcracks occur to decrease the strength. In addition, the increase of the cristobalite crystal phase cause the decrease of the light transmittance (it becomes opaque) to decrease optical properties.

JP2007-501098 discloses a lithium disilicate-appetite glass ceramic including lithium disilicate as a main crystal phase and appetite as other crystal phase. The translucency of glass ceramic is increased by incorporating transition metal oxide in composition (it becomes opaque), and the translucency is decreased by crystallization of the appetite (it becomes transparent). In addition, in this prior art document, it is described that it is possible to adjust the translucency by these opposite effects.

In these prior arts, the transparency of the glass ceramics is adjusted by precipitation of a secondary crystal phase in addition to the main crystal phase (lithium disilicate and/or lithium metasilicate). Specifically, the transparency is changed by the difference in the refractive index between the precipitated crystal and the residual glass phase other than the crystal. Desired transparency is achieved by the quantity of the crystal phase.

There are some kinds in a preparation method of a dental crown restorative material using lithium silicate grass ceramics, and transparency adjustment is necessary depending on the method and the restored portion. Specific examples of the method include a stain method in which an enamel portion is prepared from lithium silicate glass ceramics and is finished with stain and the like, a cut back method in which a dentin portion is prepared from lithium silicate glass ceramics and an enamel portion is built-up by using an upper layer porcelain, and a layering method in which the coping is prepared from lithium silicate glass ceramics and an enamel portion and a dentin portion are built-up by using an upper layer porcelain.

Among them, the layering method which uses a coping can provide reproduce an arbitrary color tone by the upper layer porcelain and therefore can provide a dental crown restorative material having high aesthetic property.

However, when the transparency adjustment of lithium silicate glass ceramics used in the layering method is insufficient, it may be difficult to prepare a dental crown restorative material having high aesthetic property because of effect from the abutment tooth which is discolored due to the transparency. It is necessary to prepare glass ceramics having high shielding property for completely shielding the abutment tooth color. It is possible to improve the shielding property by the difference in the refractive index between the crystal in the glass and the residual glass phase other than crystal. However, there is a limit on shielding property improvement, and it is impossible to shield the abutment tooth color completely. The large composition adjustment for improving the shielding property causes the decrease of the strength and the defective molding of the tooth crown restorative material, and therefore a characteristic of glass ceramic required in a tooth crown restorative material is lost.

Thus, when high shielding property is achieved, material strength decreases, and when material strength is prioritized, high shielding property is not provided. As described above, lithium silicate grass ceramics having high shielding property and high strength have not been provided due to the effect of crystal contained in the conventional lithium silicate grass ceramics.

SUMMARY OF THE INVENTION

Technical Problem

The transparency of glass ceramics varies depend on the difference in the refractive index between the precipitated crystal and the residual glass phase other than crystal. Depending on the kind of the crown restorative material, because of effect from the abutment tooth due to the transparency, the preparation of a dental crown restorative material having high aesthetic property is prevented. Although it is possible to adjust the composition of lithium silicate glass in order to adjust the refractive index, because there is a limit on the adjustment, and the large composition adjustment causes the decrease of the strength and the defective molding of the tooth crown restorative material.

Therefore, the present invention provides a dental lithium silicate glass ceramics having high shielding property and high strength in which a main crystal phase (lithium disilicate and/or lithium metasilicate) and a secondary crystal phase (single crystal and/or composite crystal of a tetravalent metal oxide) are precipitated efficiently from the dental lithium silicate composition consisting of the specific oxide containing composition after heat treatment. In this way, a tooth crown restorative material having high aesthetic property without the effect of the abutment tooth color.

Solution to Problem

The present inventors made a diligent study in order to achieve the above-described object, and consequently have proposed the present invention by discovering that a secondary crystal phase (single crystal and/or composite crystal of a tetravalent metal oxide) is precipitated efficiently from a dental lithium silicate glass composition having specific oxide content ranges after heat treatment in addition to a main crystal (lithium disilicate and/or lithium metasilicate) including needle-like forms, to adjust the transparency of the dental lithium silicate glass ceramics. In the prior art, there is a limit on the transparency adjustment of the glass ceramics by the difference in the refractive index between the precipitated crystal in the glass and the residual glass phase other than crystal, and the large composition adjustment causes the decrease of the strength. However, in the present invention, while maintaining glass stability, chemical durability and high strength, transparency adjustment of the lithium silicate glass ceramics is succeeded by precipitating single crystal and/or composite crystal of a tetravalent metal oxide as a secondary crystal. Moreover, in the conventional dental lithium silicate glass ceramics after heat treatment, only the main crystal (lithium disilicate and/or lithium metasilicate) is precipitated. Therefore, the refractive index difference between the crystal and the glass matrix surrounding the crystal is small, and hence the conventional dental lithium silicate glass ceramics have high transparency. In the present invention, because a secondary crystal (single crystal and/or composite crystal of a tetravalent metal oxide) is precipitated in addition to the glass matrix and main crystal (lithium disilicate and/or lithium metasilicate), the refractive index difference between the main crystal and the glass matrix is increased. As a result, the shielding property of the lithium silicate glass ceramics after crystallization can be improved.

That is, the dental lithium silicate glass composition of the present invention is an $Al_2O_3$-free dental lithium silicate glass composition comprising the following components:
$SiO_2$: 60.0 to 80.0% by weight
$Li_2O$: 10.0 to 17.0% by weight
$K_2O$: 0.5 to 10.0% by weight
a nucleating agent: 1.0 to 6.0% by weight
a colorant: 0.0 to 10.0% by weight, and,
a metal oxide Me(tetravalent)$O_2$: 5.0 to 10.0% by weight.

It is preferable that the dental lithium silicate glass composition of the present invention is the $Al_2O_3$-free dental lithium silicate glass composition consists of the following components:
the $SiO_2$: 60.0 to 80.0% by weight
the $Li_2O$: 10.0 to 17.0% by weight
the $K_2O$: 0.5 to 10.0% by weight
the nucleating agent: 1.0 to 6.0% by weight
the colorant: 0.0 to 10.0% by weight, and,
the metal oxide Me(tetravalent)$O_2$: 5.0 to 10.0% by weight.

It is preferable that the dental lithium silicate glass composition of the present invention is the dental lithium silicate glass composition, wherein, the metal oxide Me(tetravalent)$O_2$ is one of more kinds selected from the group consisting of $TiO_2$, $ZrO_2$, $SnO_2$, $HfO_2$, $PbO_2$, $CeO_2$ and the mixture thereof.

A dental lithium silicate glass ceramic of the present invention is a dental lithium silicate glass ceramic comprising a heat treated product of the glass composition of the present invention, wherein the precipitate of a lithium metasilicate crystal and/or a lithium disilicate crystal is included as a main crystal phase, and the precipitate of a single crystal and/or a composite crystal of a tetravalent metal oxide is included as a secondary crystal phase.

In the present disclosure, "main crystal phase" refers to a crystal phase having the highest volume ratio as compared with other crystal phases. Further, "secondary crystal phase" refers to a crystal phase other than the main crystal phase.

The dental crown restorative material of the present invention is a dental crown restorative material prepared by at least one method of thermocompression molding, mechanical processing and building up/firing of a glass ceramic of the present invention or a glass ceramic obtained by heat treating the lithium glass composition of the present invention.

DETAILED DESCRIPTION OF THE PREFERRED EMBODIMENTS

Hereinafter, the dental lithium silicate glass composition of the present invention is described in detail.

The dental lithium silicate glass composition of the present invention is an $Al_2O_3$-free dental lithium silicate glass composition comprising the following components,
$SiO_2$: 60.0 to 80.0% by weight
$Li_2O$: 10.0 to 17.0% by weight
$K_2O$: 0.5 to 10.0% by weight
a nucleating agent: 1.0 to 6.0% by weight
a colorant: 0.0 to 10.0% by weight, and,
a metal oxide Me(tetravalent)$O_2$: 5.0 to 10.0% by weight.

By adopting such a composition, main crystal (lithium disilicate and/or lithium metasilicate) and secondary crystal (single crystal and/or composite crystal of a tetravalent metal oxide) can be precipitated efficiently and in a high density after heat treatment, and a high shielding property of the dental lithium silicate glass ceramics can be achieved. In the present invention, an $Al_2O_3$-free dental lithium silicate glass composition includes, within the scope of the present invention, even any case where a dental lithium silicate glass composition includes $Al_2O_3$ as an impurity within a range of less than 0.1% by weight range. Accordingly, the analytical measurement method of the $Al_2O_3$ content is not particularly limited, but the case where by any one of analytical measurement methods, the $Al_2O_3$ content of less than 0.1% by weight as an impurity is found is included in the category of the dental lithium silicate glass composition of the present invention. That is, the dental lithium silicate glass composition of the present invention is a substantially $Al_2O_3$-free dental lithium silicate glass composition, or a dental lithium silicate glass composition including the following components:

$SiO_2$: 60.0 to 80.0% by weight
$Li_2O$: 10.0 to 17.0% by weight
$K_2O$: 0.5 to 10.0% by weight
a nucleating agent: 1.0 to 6.0% by weight
a colorant: 0.0 to 10.0% by weight,
a metal oxide Me(tetravalent)$O_2$: 5.0 to 10.0% by weight, and
$Al_2O_3$: 0.0 to 0.1% by weight. It is preferable that a dental lithium silicate glass composition of the present invention does not include $Al_2O_3$ perfectly. It is also preferable that a dental lithium silicate glass composition of the present invention consists of the following components, wherein $Al_2O_3$ is not included:

$SiO_2$: 60.0 to 80.0% by weight
$Li_2O$: 10.0 to 17.0% by weight
$K_2O$: 0.5 to 10.0% by weight
a nucleating agent: 1.0 to 6.0% by weight
a colorant: 0.0 to 10.0% by weight, and,
a metal oxide Me(tetravalent)$O_2$: 5.0 to 10.0% by weight.

The oxide contents of the respective components in the above-described dental lithium silicate glass composition of the present invention are independent of each other, and composed of the following essentially specified components.

The $SiO_2$ included in the dental lithium silicate glass composition of the present invention functions as a glass-forming oxide during glass melting, and after heat treatment, functions as the component of the main crystal (lithium disilicate and/or lithium metasilicate) and a component of the glass phase surrounding the main crystal.

When the $SiO_2$ content in the dental lithium silicate glass composition of the present invention is within a range from 60.0 to 80.0% by weight, $SiO_2$ can be used without causing any problems, and the $SiO_2$ content is more preferably within a range from 60.0 to 75.0% by weight. When the $SiO_2$ content is less than 60.0% by weight, no sufficient glass phase can be formed, the durability of the glass is degraded, the proportion of the main crystal (lithium disilicate and/or lithium metasilicate) precipitated after heat treatment is concurrently varied, thus no appropriate amount of the main crystal (lithium disilicate and/or lithium metasilicate) is precipitated, and no high material strength is obtained. In addition, when the $SiO_2$ content is larger than 80.0% by weight, the glass phase is increased to improve the durability of the glass phase, but no sufficient main crystal (lithium disilicate and/or lithium metasilicate) are precipitated, the crystallization of $SiO_2$ as a single substance disturbs the precipitation of the main crystal, and hence no high material strength is obtained.

The $Li_2O$ included in the dental lithium silicate glass composition of the present invention functions as a frit during glass melting, promotes the achievement of low-temperature melting of glass, and also functions as a component of the main crystal (lithium disilicate and/or lithium metasilicate) precipitated by heat treatment. When the $Li_2O$ content in the dental lithium silicate glass composition of the present invention is within a range from 10.0 to 17.0% by weight, $Li_2O$ can be used without causing any problems, and the $Li_2O$ content is more preferably within a range from 12.0 to 17.0% by weight.

When the $Li_2O$ content is less than 10.0% by weight, the frit is small in amount and glass cannot be melted. In addition, because the proportion of the main crystal to be precipitated after heat treatment is varied, no appropriate amount of the main crystal (lithium disilicate and/or lithium metasilicate) is precipitated, and thus no high material strength is obtained. When the $Li_2O$ content is larger than 17.0% by weight, no stable glass phase can be formed, the durability of the glass is degraded, the proportion of the main crystal precipitated after heat treatment is concurrently varied, and no high material strength is obtained.

The $K_2O$ included in the dental lithium silicate glass composition of the present invention functions as the frit during glass melting, promotes the low melting of the glass, and concurrently promotes the crystallization of the main crystal (lithium disilicate and/or lithium metasilicate) precipitated by heat treatment. When the $K_2O$ content in the dental lithium silicate glass composition of the present invention is within a range from 0.5 to 10.0% by weight, $K_2O$ can be used without causing any problems, and the $K_2O$ content is more preferably within a range from 2.0 to 8.0% by weight.

When the $K_2O$ content is less than 0.5% by weight, the amount of the frit is small, and hence the glass cannot be melted. In addition, the crystallization of the main crystal (lithium disilicate and/or lithium metasilicate) precipitated after heat treatment is suppressed, and hence no high material strength is obtained. When the $K_2O$ content is larger than 10.0% by weight, no stable glass phase can be formed, the durability of the glass is degraded, the precipitation of the main crystal precipitated after heat treatment is concurrently disturbed, and hence no high material strength is obtained.

It is possible to use, without being particularly limited, any nucleating material included in the dental lithium silicate glass composition of the present invention, functioning as a generation origin of the main crystal (lithium disilicate and/or lithium metasilicate) precipitated by heat treatment. Specific examples of these nucleating agents include: $P_2O_5$, $WO_3$, $V_2O_5$, Pt and Ag. Among these nucleating agents, a particularly effective nucleating agent is $P_2O_5$. At least one of these nucleating agent is mixed, but combinations of two or more of these can also be mixed. By using $P_2O_5$ as the nucleating agent, it may be possible to deposit a fine $Li_3PO_4$ (lithium phosphate) which acts as the origin of the main crystal (lithium disilicate and/or lithium metasilicate), therefore it may be possible to deposit the main crystal (lithium disilicate and/or lithium metasilicate) effectively.

The nucleating agent content in the dental lithium silicate glass composition of the present invention is within a range from 1.0 to 6.0% by weight, the nucleating agent can be used without causing any problems, and the nucleating agent content is more preferably within a range from 1.0 to 5.0% by weight. When the nucleating agent content is less than 1.0% by weight, the coarsening of the main crystal and the degradation of the transparency are caused, and no sufficient transparency and no high material strength can be obtained. When the nucleating agent content is larger than 6.0% by weight, the increase of the crystal amount and the refinement of the crystal are promoted, but the glass phase remaining after the crystallization is decreased, and thus the durability of the glass is degraded.

It is possible to use, without being particularly limited, any colorant included in the dental lithium silicate glass composition of the present invention, functioning as a color tone conditioner for approximating to natural teeth (dentin and enamel). Specific examples of these colorants include: MnO, $Fe_2O_3$, $Tb_4O_7$, $Eu_2O_3$, $Ni_2O_3$, $Cr_2O_3$, $Co_2O_3$, $Nd_2O_3$, $Pr_6O_{11}$, $Sm_2O_3$, $V_2O_5$, $Dy_2O_3$, $Ho_2O_3$ and $Er_2O_3$. In addition, natural teeth exhibit fluorescent colors by the irradiation of ultraviolet light, and accordingly, it is preferable that these colorants exhibit fluorescent colors. These colorants can be appropriately selected according to the color tone of the dental crown restorative material, and if necessary, one or combinations of two or more thereof can be mixed.

When the colorant content in the dental lithium silicate glass composition of the present invention is within a range from 0.0 to 10.0% by weight, the colorant can be used without causing any problems, and the colorant content is more preferably within a range from 0.5 to 10.0% by weight. When the contents of these colorants are each larger than 10.0% by weight, an abundant color tone conditioning can be performed, but the precipitation of the main crystal (lithium disilicate and/or lithium metasilicate) is disturbed, and hence no high material strength is obtained. When the colorant is not included, it can be applied to a tooth crown color with no coloration and therefore it is preferable.

The metal oxide Me(tetravalent)$O_2$ contained in the dental lithium silicate glass composition of the present invention precipitates a single crystal and/or a composite crystal after heat-treatment. Specific examples of these metal oxides Me(tetravalent)$O_2$ include $TiO_2$, $ZrO_2$, $SnO_2$, $HfO_2$, $PbO_2$ and $CeO_2$. When the content is within a range from 5.0 to 10.0% by weight, the metal oxide Me(tetravalent)$O_2$ can be used without causing any problems, and the content is more preferably within a range from 6.0 to 9.0% by weight.

When the content of the metal oxide Me(tetravalent)$O_2$ is less than 5.0% by weight, a secondary crystal phase does not precipitate after heat-treatment. Therefore, because the difference in the refractive index between the crystal phase and the glass phase becomes smaller, the shielding property decreases. When the content of the metal oxide Me(tetravalent)$O_2$ is larger than 10.0% by weight, the difference in the refractive index between the crystal phase and the glass phase becomes larger, therefore the shielding property is improved, but no sufficient main crystal (lithium disilicate and/or lithium metasilicate) are precipitated during the heat treatment, and hence no high material strength is obtained.

The metal oxide Me(tetravalent)$O_2$ can increase the difference in the refractive index between the crystal phase and the glass phase after the crystallization (make opaque) and improve the shielding property. The refractive index of the lithium disilicate crystal is within a range of 1.56 to 1.57 and the refractive index of the glass phase depends on the refractive index of the component which does not concern the crystallization. The refractive index of the metal oxide Me(tetravalent)$O_2$ in the dental lithium silicate glass composition of the present invention is larger than that of the lithium disilicate crystal and is within a range of 1.94 to 2.30. These ingredients become a single crystal and/or a composite crystal to increase the refractive index. Therefore, the shielding property increases with the increase of the difference of the refractive index between the lithium disilicate crystal.

The dental lithium silicate glass composition of the present invention does not include $Al_2O_3$. In the case where a lithium silicate glass composition of the present invention includes $Al_2O_3$, in addition to the main crystal (lithium disilicate and/or lithium metasilicate) precipitated from the lithium silicate glass composition, various crystals (such as lithium aluminum silicate compounds including spodumene) are precipitated by heat treatment through the reaction with $Li_2O$ in the composition, accordingly the degradation of the material strength is caused. Further, because the refractive index of the lithium aluminum silicate compounds is approximate to the refractive index of the lithium disilicate crystal, the difference in the refractive index becomes small to decrease the shielding property. As a result, high material strength and shielding property which are required for a dental glass ceramics cannot be exhibited. When $P_2O_5$ is added as a nucleating agent in the lithium silicate glass composition, $Al_2O_3$ and $P_2O_5$ in the composition react with each other by heat treatment and crystals such as aluminum phosphate are also precipitated, and hence the addition of $P_2O_5$ as a nucleating agent further promotes the degradation of the material strength and the shielding property.

The method for preparing the dental lithium silicate glass composition of the present invention is not particularly limited, and any preparation method can prepare the foregoing dental lithium silicate glass composition. Specific examples of the preparation method concerned include: a method in which the glass raw materials are mixed, and then melted at a high temperature, and a method (sol-gel method) in which organic compounds or inorganic compounds are dissolved in a solvent, and are allowed to react in the resulting solution and then the solvent is volatilized; it is preferable to use the glass melting method from the viewpoint of the easiness of the glass composition design, the preparation amount, the preparation facilities, the cost and others. The preparation conditions in the glass melting method, such as the feeding temperature of the glass raw materials, the temperature increase rate, the melting temperature and the holding time are not particularly limited; as long as the preparation conditions allow to obtain a melt in which the glass materials are uniformly melted, the preparation conditions are not particularly limited. In particular, the dental lithium silicate glass composition of the present invention is preferably melted within a range from 1200° C. to 1650° C.

Moreover, the dental lithium silicate glass composition of the present invention is not particularly limited with respect to the shape thereof, and can be regulated so as to have various shapes such as a powdery shape, a granular shape, a plate-like shape (frit) and a glass block shape (glass blank). The glass block shape (glass blank) can be prepared by casting the above-described melt into, for example, a carbon, metal or ceramic mold, and by slowly cooling the melt down to room temperature.

The glass blank (columnar shape or prismatic shape) can also be molded by filling under pressurization the glass melt into a mold in a high viscosity state (at a temperature of 700° C. to 1200° C.) achieved by controlling the viscosity of the glass melt. A plate-like shape (frit) can be prepared by dropping the above-described melt between internally cooled two rolls and thus by rapidly cooling the melt. The granular shape can be prepared by placing in a whirling manner the above-described melt into cooled running water.

The powdery shape can be obtained by pulverizing these shapes by using, for example, a pulverizer. The shapes of the dental lithium silicate glass composition can be appropriately regulated, for example, by the preparation method based on the heat treatment as the subsequent step, or by the preparation method in the case of the preparation of a dental crown restorative material.

As a feature of the present invention, the present invention is capable of preparing dental lithium silicate glass ceramics by efficiently and highly densely precipitating the main crystal (lithium disilicate and/or lithium metasilicate) and the secondary crystal (single crystal and/or composite crystal of a tetravalent metal oxide) through the heat treatment of the dental lithium silicate glass compositions having various shapes. The heat treatment is an important step because the heat treatment can control the precipitation proportion of the main crystal (lithium disilicate and/or lithium metasilicate) and the secondary crystal (single crystal and/or composite crystal of a tetravalent metal oxide) precipitated after the heat treatment. The heat treatment conditions for heat treating the dental lithium silicate glass composition of the present invention, such as the heat treatment starting temperature, the temperature increase rate, the heat treatment temperature, the heat treatment holding time, and the annealing temperature are not particularly limited, and can be appropriately selected according to, for example, the shape of the dental lithium silicate glass composition to be heat treated, the method for preparing a dental crown restorative material, and the control of the precipitation conditions of the crystal. Among these, the heat treatment temperature is a particularly important item because of being capable of controlling the precipitation proportion of the main crystal (lithium disilicate and/or lithium metasilicate) and the secondary crystal (single crystal and/or composite crystal of a tetravalent metal oxide), and the heat treatment is preferably performed at a heat treatment temperature falling within a range from 450 to 950° C. When the heat treatment temperature is lower than 450° C., there is a case where the dental lithium silicate glass composition of the present invention cannot be fired or crystallized. When the heat treatment temperature is higher than 950° C., there is a case where the forms of the precipitated main crystal (lithium disilicate and/or lithium metasilicate) are collapsed due to the nature of the dental lithium silicate glass composition of the present invention. Accordingly, it is preferable that the heat treatment temperature should not deviate from this temperature range.

On the other hand, preferably, the heat treatment starting temperature is 450° C. to 550° C., the temperature increase rate is 10° C. to 50° C./min, and the annealing rate is 10° C. to 20° C./min. The starting temperature of the heat treatment is preferably in the vicinity of the glass transition point for the purpose of appropriately precipitating the main crystal. The temperature increase rate is preferably such that the temperature is more slowly increased because the crystallization is required to be more stably promoted. The annealing rate has little effect on the crystal precipitation; however, when a rapid cooling is performed, cracks might occur in the glass, and hence a slow cooling is preferable.

The lithium metasilicate crystal precipitated from the dental lithium silicate glass composition of the present invention has a tendency to be precipitated within a heat treatment temperature range from 580° C. to 780° C., the crystal is very fine and has various crystal forms, and hence the dental lithium silicate glass composition has the features that the material strength and the ductility are both low and the processability is excellent. On the other hand, the lithium disilicate crystal precipitated from the dental lithium silicate glass composition of the present invention has a tendency to be precipitated within a heat treatment temperature range from 800° C. to 920° C., this crystal has a large size as compared with the above-described lithium metasilicate crystal and exhibits a needle-like form, these crystals are precipitated in a high density and have a structure in which these crystals are entangled with each other, and hence the dental lithium silicate glass composition has the features that the development of the cracks is suppressed and high material strength is developed. The secondary crystal (single crystal and/or composite crystal of a tetravalent metal oxide) precipitated from the dental lithium silicate glass composition of the present invention has a tendency to be precipitated within a heat treatment temperature range from 770° C. to 930° C., the precipitation of this crystal can increase the difference in the refractive index between the glass phase and the crystal phase to improve the shielding property. The precipitation temperature of the crystal precipitated from the dental lithium silicate glass composition of the present invention can be verified from the exothermic peak of the TG-DTA, and the crystal can be identified by X-ray diffraction.

It is also an effective method to regulate the holding time within the heat treatment temperature range allowing the above-described respective crystals (lithium disilicate and lithium metasilicate) and the secondary crystal (single crystal and/or composite crystal of a tetravalent metal oxide) to be precipitated, for the purpose of efficiently precipitate these crystals in high densities. Specifically, as the heat treatment of the dental lithium silicate glass composition of the present invention, preferable is a two-stage heat treatment in which the composition is held for a certain period of time at the heat treatment temperature allowing the lithium metasilicate to be precipitated, then the temperature is slowly increased to the heat treatment temperature allowing the lithium disilicate to be precipitated and the composition is held for a certain period of time, then the composition is slowly cooled; it is more preferable to perform a three-stage heat treatment including before such a two-stage treatment, a nucleation heat treatment performing a holding for a certain period of time within a range from 450° C. to 550° C. The nucleation heat treatment aims at the formation of the generation origin of the main crystal precipitated from the dental lithium silicate glass composition of the present invention, and is an effective method for precipitating the crystal efficiently and in a high density.

There is no particular limitation on the shape of the lithium silicate glass ceramics prepared by precipitating the main crystal (lithium disilicate and/or lithium metasilicate) and the secondary crystal (single crystal and/or composite crystal of a tetravalent metal oxide) through the heat treatment of the dental lithium silicate glass composition of the present invention; the shape of the dental lithium silicate glass ceramic can be selected according to the step for preparing the dental crown restorative material. For example, a glass agglomerated state is taken by the lithium silicate glass ceramic allowed to precipitate the main crystal (lithium disilicate and/or lithium metasilicate) and the secondary crystal (single crystal and/or composite crystal of a tetravalent metal oxide) by heat treating a powdery, granular or plate-like dental lithium silicate glass composition; however, by pulverization processing of these agglomerates, a powdery lithium silicate glass ceramic can be prepared. The average particle size of the resulting powdery ceramics is 1 to 100 μm, and preferably 10 to 50 μm. The powdery dental lithium silicate glass composition is filled in a mold and compressed to form a molded article (columnar shape or prismatic shape), the molded article is heat treated to precipitate the main crystal (lithium disilicate and/or lithium metasilicate) and the secondary crystal (single crystal and/or composite crystal of a tetravalent metal oxide), and thus a blank (columnar shape or prismatic shape) of the lithium silicate glass ceramic can be prepared. Moreover, the glass blank (columnar shape or prismatic shape) of the dental lithium silicate glass composition is not pulverized and heat treated as it is, consequently the main crystal (lithium disilicate and/or lithium metasilicate) and the secondary crystal (single crystal and/or composite crystal of a tetravalent metal oxide) are precipitated, and thus a blank (columnar shape or prismatic shape) of the lithium silicate glass ceramics can be prepared. As described above, the dental lithium silicate glass composition of the present invention is molded into various shapes, the resulting various shapes are heat treated, and thus the lithium silicate glass ceramics having various shapes can be prepared; however, the shapes of the dental lithium silicate glass ceramics are not limited to such shapes as de scribed above.

From the dental lithium silicate glass ceramic obtained by heat treating the dental lithium silicate glass composition, it is possible to prepare a dental crown restorative material by at least one preparation method of thermocompression molding, mechanical processing and building up/firing. For example, a powdery heat-treated dental lithium silicate glass ceramics is mixed with a malaxation liquid, then the resulting mixture is built up on a base while the mixture is being condensed, thus a form of the dental crown restorative material is reproduced and then fired, and consequently a dental crown restorative material can be prepared. The blank of the dental lithium silicate glass ceramic obtained by heat treatment is softened by using a special press molding device under heating and pressurization conditions, then the blank is pressed into a mold deprived of wax by firing, and thus a dental crown restorative material can be prepared. Moreover, the blank of the dental lithium silicate glass ceramic obtained by heat treatment is subject to cutting and machining by using a computer-controlled cutting and machining machine, and thus a dental crown restorative material can also be prepared.

In the preparation of the dental crown restorative material by the cutting and machining device, by taking the differences in the precipitation temperatures of the main crystal (lithium disilicate and lithium metasilicate) precipitated from the above-described dental lithium silicate glass composition of the present invention, the dental crown restorative material can be efficiently prepared. Specifically, lithium metasilicate crystal is mainly precipitated by controlling the temperature of the heat treatment, to improve machinability. This is a preparation method in which: a lithium silicate glass ceramic is machined into a desired shape of the dental crown restorative material; and then the machined dental crown restorative material is again heat treated to precipitate lithium disilicate crystal to achieve a high strength.

Hereinafter, there are shown specific examples of a series of processes from the preparation of the dental lithium silicate glass composition of the present invention, through the preparation of the dental lithium silicate glass ceramic obtained by heat treating the glass composition, to the preparation of the dental crown restorative material using the dental lithium silicate glass ceramic, but not limited to these examples.

[Preparation Process 1]
1-A Step: Preparation of a Dental Lithium Silicate Glass Composition
(1-A-1) A step in which the glass raw materials (carbonates/oxides and colorant oxide) are mixed, and then the resulting mixture is melted in a temperature range from 1200° C. to 1650° C.
(1-A-2) A step in which the molten glass melt is filled as it is in a mold, and a glass blank (columnar shape or prismatic shape) is formed.
1-B Step: Preparation of a Lithium Silicate Glass Ceramic
(1-B1) A step in which the glass blank is heat treated at least once in a range from 500° C. to 950° C.
1-C Step: Preparation of a Dental Crown Restorative Material
(1-C-1) A step in which the lithium silicate glass ceramic of the heat-treated glass blank is heated and softened at a temperature of 500° C. to 1200° C., then pressed into the clearance of the investment material mold under a pressure of approximately 0.1 to 1 MPa, and thus a dental crown restorative material having a desired form (bridge or crown) is preparation.

[Preparation Process 2]
2-A Step: Preparation of a Dental Lithium Silicate Glass Composition
(2-A-1) A step in which the glass raw materials (carbonates/oxides and colorant oxide) are mixed, then the resulting mixture is melted in a temperature range from 1200° C. to 1650° C.
(2-A-2) A step in which the molten glass melt is filled as it is in a mold, and a glass blank (columnar shape or prismatic shape) is formed.
2-B Step: Preparation of a Dental Lithium Silicate Glass Ceramic
(2-B-1) A step in which the glass blank is at least once heat treated in a range from 500° C. to 780° C.
2-C Step: Preparation of a Dental Crown Restorative Material
(2-C-1) A step in which the lithium silicate glass ceramic of the heat treated glass blank is subject to cutting and machining by using a computer-controlled cutting and machining to prepare a desired form (bridge or crown), the cut and machined article is at least once heat treated in a temperature range from approximately 700° C. to 950° C. for between approximately 5 to 30 minutes, and thus a dental crown restorative material is prepared.

[Preparation Process 3]
3-A Step: Preparation of a Dental Lithium Silicate Glass Composition
(3-A-1) A step in which the glass raw materials (carbonate/oxide) are mixed, and then the resulting mixture is melted in a temperature range from 1200° C. to 1650° C.
(3-A-2) A step in which the molten glass melt is cooled, and thus a granular glass material or a glass plate (frit) is formed.
3-B Step: Preparation of a Dental Lithium Silicate Glass Ceramic
(3-B-1) A step in which the granular glass material or the glass plate is heat treated at least once in a range from 500° C. to 780° C.
(3-B-2) A step in which the heat treated granular glass material or the heat treated glass plate is pulverized to a powder having an average particle size of 10 to 50 μm.
(3-B-3) A step in which the pulverized powder and the colorant oxide are mixed.

(3-B-4) A step in which the above-described mixture powder is packed in a mold having a desired shape, and thus a molded article, a glass blank having a non-uniform structure, is formed.

(3-B-5) A step in which the molded article is subjected to a heat treatment in a temperature range from 400° C. to 950° C. under vacuum, and thus a dense glass ceramic blank is formed.

3-C Step: Preparation of a Dental Crown Restorative Material (3-C-1) A step in which the lithium silicate glass ceramic having a blank shape is heated and softened at a temperature of 500° C. to 1200° C., then pressed into the clearance of the investment material mold under a pressure of approximately 0.1 to 1 MPa, and thus a dental crown restorative material having a desired form (bridge or crown) is prepared.

[Preparation Process 4]

4-A Step: Preparation of a Dental Lithium Silicate Glass Composition (4-A-1) A step in which the glass raw materials (carbonates/oxides) are mixed, and then the resulting mixture is melted in a temperature range from 1200° C. to 1650° C.

(4-A-2) A step in which the molten glass melt is cooled, and thus a granular glass material or a glass plate (frit) is formed.

4-B Step: Preparation of a Dental Lithium Silicate Glass Ceramic (4-B-1) A step in which the granular glass material or the glass plate (frit) is heat treated at least once in a range from 500° C. to 780° C.

(4-B-2) A step in which the heat treated granular glass material or the heat treated glass plate (frit) is pulverized to a powder having an average particle size of 10 to 50 μm.

(4-B-3) A step in which the pulverized powder and the colorant oxide are mixed.

(4-B-4) A step in which the above-described mixture powder is packed in a mold having a desired shape, and thus a molded article, a glass blank having a non-uniform structure, is formed.

(4-B-5) A step in which the molded article is subjected to a heat treatment in a temperature range from 400° C. to 950° C. under vacuum, and thus a dense glass ceramic blank is formed.

4-C Step: Preparation of a Dental Crown Restorative Material (4-C-1) A step in which the lithium silicate glass ceramic having a blank shape is subject to cutting and machining by using a computer-controlled cutting and machining machine to prepare a desired form (bridge or crown), the cut and machined article is at least once heat treated in a temperature range from approximately 700° C. to 950° C. for between approximately 5 to 30 minutes, and thus a dental crown restorative material is prepared.

[Preparation Process 5]

5-A Step: Preparation of a Dental Lithium Silicate Glass Composition (5-A-1) A step in which the glass raw materials (carbonates/oxides and colorant oxide) are mixed, and then the resulting mixture is melted in a temperature range from 1200° C. to 1650° C.

(5-A-2) A step in which the molten glass melt is cooled, and thus a granular glass material or a glass plate (frit) is formed.

5-B: Preparation of a Dental Lithium Silicate Glass Ceramic (5-B-1) A step in which the granular glass material or the glass plate (frit) is heat treated at least once in a range from 500° C. to 780° C.

(5-B-2) A step in which the heat treated granular glass material or the heat treated glass plate (frit) is pulverized to a powder having an average particle size of 10 to 50 μm.

(5-B-3) A step in which the pulverized powder and the colorant oxide are mixed.

5-C Step: Preparation of a Dental Crown Restorative Material (5-C-1) A step in which the dental lithium silicate glass ceramic, a powder after heat treatment, mixed with a colorant, is mixed with a malaxation liquid; then the resulting mixture is built up on a base prepared from a zirconia and lithium silicate-based glass ceramic while the mixture is being condensed; and the built-up mixture is fired by using a firing furnace in a range from 500° C. to 950° C.; and thus a dental crown restorative material, having a desired form (bridge or crown) is prepared.

The above-described dental crown restorative material (such as a bridge or a crown) prepared from the lithium silicate glass ceramic of the present invention can be finished with a color tone approximating to the natural teeth and aesthetically, by finally performing a coloration with a staining material or the coating of the surface layer with a glaze material. Examples of such a staining material and such a glaze material include, without being limited to: a ceramic, a sintered ceramic, a glass ceramic, a glass, a glaze and/or composite materials. The staining material is used as a color tone conditioner for mimicking the color tone of the natural teeth, and the glaze material is used for improving the smoothness and shine and the glossiness of the surface. Among these staining materials and these glaze materials, preferable are the staining materials and the coating materials capable of being fired in a temperature range from 650° C. to 950° C., and having the coefficient of thermal expansion difference, from the coefficient of thermal expansion of the dental crown restorative material prepared from the lithium silicate glass ceramic of the present invention, falling within a range of $1.0\pm0.5\times10^{-6}K^{-1}$.

As described above, the dental lithium silicate glass ceramic appropriately formed by using the dental lithium silicate glass composition of the present invention can be used clinically as an inlay, an onlay, a coping, a crown, a bridge, a post, a facing crown, a jacket crown, a laminate veneer and splinted crowns, and preferably as a coping a facing crown, a jacket crown.

EXAMPLES

The present invention is described in dental on the basis of following Examples. However, the present invention is not limited to the scope of these Examples. The test methods adopted in Examples and Comparative Examples are as follows.

[Evaluation Methods]

(1) The Bending Strength (Three Point Bending) Test

The bending strength (three point bending) test was performed according to ISO 6872 Dentistry—Ceramic Materials.

(2) Solubility Test

The solubility was performed according to ISO 6872 Dentistry—Ceramic Materials.

(3) Contrast Ratio Measurement

Round plates (φ14.0 mm×2.0 mm) were prepared by using the dental lithium silicate glass ceramics of respective Examples and Comparative Examples; samples regulated to be 1 mm in thickness were subjected to a color measurement (white background and black background) by using a spectrocolorimeter, and the contrast ratios were calculated from the color measurement data.
Calculation formula: (Contrast ratio)=(Y value of black background colorimetry)/(Y value of white background colorimetry)
Measurement apparatus: CM-3500d (manufactured by Konica Minolta Holdings, Inc.)
(4) Verification of Crystal System
The dental lithium silicate glass ceramics of respective Examples and Comparative Examples were pulverized, and the crystal systems of the crystal precipitated in the heat treatments of the respective stages were verified by XRD. The abbreviations in the table mean as follows: LDS: lithium disilicate, LMS: lithium metasilicate, LP: lithium phosphate, and TC: single crystal and/or composite crystal of a tetravalent metal oxide.
Apparatus used: Multiflex (Rigaku Corp.)
Measurement condition: Scanning range 10° to 70°, scanning speed: 2.0°/min
(5) Test of Seizure to Investment Material
The lithium silicate glass ceramics blank of respective Examples and Comparative Examples were softened under heated and pressurized condition by using press molding apparatus and pressed into a mold from which a round plate (φ14.0 mm×1.4 mm) made of a wax was removed by firing, and thus the specimens were prepared. Subsequently, the investment material of each of the press molded specimens was removed with an alumina sand blast (alumina particle size: 110 μm, pressure: 0.4 MPa), the surface of each of the specimens after removal of the investment material was visually observed, and thus the removal state of the investment material was evaluated.
Investment material: Ceravety Press & Cast (manufactured by Shofu Inc.)
Press molding apparatus: Estemat Press (manufactured by Shofu Inc.)
[Crystal Heat Treatment Temperature]
First, the precipitation temperature (lithium disilicate and lithium metasilicate) of the dental lithium silicate glass composition of the present invention is specified by the precipitation temperature of the main crystal (lithium disilicate and lithium metasilicate) precipitated in Example 1.
The dental lithium silicate glass composition described in Table 1: The glass raw material mixture corresponding to Example 1 was maintained at 1450° C. for 1 hour to be melted. The resulting glass melt was filled in a carbon mold (φ12 mm×10 mm) preheated to 500° C., and thus a glass blank, the dental lithium silicate glass composition of the present invention, was prepared. The resulting glass blank was transparent and uniform.
In order to verify the crystal precipitation temperature of the glass blank, a TG-DTA measurement (measurement conditions: 25° C. to 1000° C. (temperature increase rate: 10° C./min)) was performed (FIG. 1). Consequently, exothermic peaks due to crystal precipitation were verified at 670° C. and 803° C. Next, the glass blank was heat treated at the temperatures of the respective exothermic peaks (starting temperature: 500° C., temperature increase rate: 10° C./min, firing temperatures: temperatures of exothermic peaks 670° C. and 803° C.), and thus the lithium silicate glass ceramics of the present invention were prepared and the precipted crystal were measured by XRD. From the obtained XRD pattern results, it was verified that the lithium metasilicate crystal was precipitated at 670° C. (FIG. 2), and the lithium disilicate crystal and the secondary crystal (single crystal and/or composite crystal of a tetravalent metal oxide) was precipitated at 803° C. (FIG. 3).
FIG. 4 shows an electron microscope observation image of the dental lithium silicate glass ceramic of the present invention heat treated at 670° C., after being subjected to an etching with 1% hydrofluoric acid for 30 seconds. From FIG. 4, it was able to be verified that the lithium metasilicate crystal disappeared due to the etching and fine traces (vacancies) of crystal were observed.
FIG. 5 shows an electron microscope observation image of the dental lithium silicate glass ceramic heat treated at 803° C., and subjected to an etching with 1% hydrofluoric acid for 3 minutes. From FIG. 5, it was able to be verified that the glassy portion disappeared, and the needle-like crystals derived from lithium disilicate were observed.
The main crystal was precipitated by subjecting, on the basis of the above-described method, the dental lithium silicate glass composition of the present invention to a heat treatment (first crystallization heat treatment (precipitation of lithium metasilicate): 660° C., second crystallization heat treatment (precipitation of lithium disilicate single crystal and/or composite crystal of a tetravalent metal oxide): 840° C.).
(Test by Press Molding)
The dental lithium silicate glass compositions, Examples 1 to 33 and the glass raw material mixtures corresponding to Comparative Examples 1 to 24 described in Tables were maintained at 1450° C. for 1 hour to be melted. The resulting glass melts were each filled in a carbon mold (φ12 mm×10 mm) preheated to 500° C., and thus glass blanks of the dental lithium silicate glass compositions of Examples 1 to 33 and the glass blanks of Comparative Examples 1 to 24 were prepared. The resulting glass blanks were each heat treated (generation of crystal nuclei) at 500° C. for 10 minutes, then subjected to a heat treatment (first crystallization heat treatment) at 660° C. for 30 minutes, and further subjected to a heat treatment (second crystallization heat treatment) at 840° C. for 30 minutes. The dental lithium silicate glass ceramics of the present invention prepared by the three staged heat treatment were used as the glass ceramic blanks for press molding.
The wax having the same shape as the shapes of the specimens used in the above-described evaluation tests (1) to (3) was embedded in the investment material (Ceravety Press & Cast, manufactured by Shofu Inc.), and the hardened mold was fired at 850° C. for 1 hour to remove the wax. In the mold after firing treatment, each of the prepared glass ceramic blanks was inserted, and was subjected to a press molding (press starting temperature: 700° C., press temperature: 920° C., holding time: 20 minutes, temperature increase rate: 60° C./min, press time: 3 minutes) by using a press molding apparatus (Estemat Press, manufactured by Shofu Inc.). In addition, when the specimens were dug out, the above-described evaluation test (5) was also performed in order to verify the condition of the seizure to the investment material. The above-described evaluation test (4) was performed in order to verify the crystal system in the final specimen.
(Test by Machining)
The dental lithium silicate glass compositions, Examples 1 to 33 and the glass raw material mixtures corresponding to Comparative Examples 1 to 24 described in Tables were maintained at 1450° C. for 1 hour to be melted. The resulting glass melts were each filled in a carbon casting mold (5 mm×22 mm×22 mm) preheated to 500° C., and thus glass blanks of the dental lithium silicate glass compositions of Examples 1 to 33 and the glass blanks of Comparative Examples 1 to 24 were prepared. The resulting glass blanks were each heat treated (generation of crystal nuclei) at 500° C. for 10 minutes, and then subjected to a heat treatment (first crystallization heat treatment) at 660° C. for 30 minutes; the glass ceramics of the present invention prepared by this two-stage heat treatment were used as the glass ceramic blanks for performing the machining.
The glass ceramic blanks were cut and machined by using a dental CAD/CAM system into the same shapes as the shapes of the specimens used in the above-described evaluation tests (1) to (3), then further subjected to a heat treatment (second crystallization heat treatment, the starting temperature: 700° C., firing temperature: 840° C., holding time: 30 minutes, temperature increase rate: 10° C./min), and thus specimens were prepared; the sizes of the specimens were regulated, and then the above-described evaluation tests (1) to (3) were performed. The above-described evaluation test (4) was also performed in order to verify the crystal system in the final specimen.

(Test by Powder Molding)

The dental lithium silicate glass compositions, Examples 1 to 33 and the glass raw material mixtures corresponding to Comparative Examples 1 to 24 described in Tables were maintained at 1450° C. for 1 hour to be melted. The resulting glass melts were each filled in a carbon casting mold (5 mm×22 mm×22 mm) preheated to 500° C., and thus glass blanks of the dental lithium silicate glass compositions of Examples 1 to 33 and the glass blanks of Comparative Examples 1 to 24 were prepared. The resulting glass blanks were each heat treated (generation of crystal nuclei) at 500° C. for 10 minutes, and then subjected to a heat treatment (first crystallization heat treatment) at 660° C. for 30 minutes; the dental lithium silicate glass ceramic blanks of the present invention prepared by this two-stage heat treatment were obtained.

The glass ceramic blanks were each pulverized to yield a dental lithium silicate glass ceramics powder of the present invention having an average particle size of 20 μm. Each of these powders was malaxated with distilled water into a slurry; each of the resulting slurries was poured into a silicon mold having the same shape as the shape of the specimen used in each of the above-described evaluation tests (1) to (3). After the moisture of each of the poured slurries was sufficiently removed, each of the molded article was released from the silicon mold, and subjected to a heat treatment (heat treatment starting temperature: 500° C., heat treatment ending temperature: 950° C., temperature increase rate: 50° C./min), and thus specimens were prepared; the sizes of the specimens were regulated, and then the above-described evaluation tests (1) to (3) were performed. The above-described evaluation test (4) was performed in order to verify the crystal system in the final specimen.

TABLE 1

| | Component | Example 1 | Example 2 | Example 3 | Example 4 | Example 5 | Example 6 |
|---|---|---|---|---|---|---|---|
| Mass Ratio (%) | $SiO_2$ | 68.7 | 60.0 | 80.0 | 73.2 | 70.9 | 67.1 |
| | $Li_2O$ | 15.3 | 16.8 | 12.1 | 10.0 | 14.5 | 17.0 |
| | $K_2O$ | 4.5 | 8.9 | 1.6 | 3.8 | 4.3 | 6.2 |
| | $P_2O_5$ | 4.0 | 5.4 | 1.3 | 4.6 | 2.9 | 2.9 |
| | $TiO_2$ | 0.0 | 0.0 | 0.0 | 0.0 | 0.0 | 0.0 |
| | $ZrO_2$ | 2.0 | 5.2 | 1.0 | 2.8 | 3.1 | 3.7 |
| | $SnO_2$ | 0.0 | 0.0 | 0.0 | 0.0 | 0.0 | 0.0 |
| | $CeO_2$ | 5.5 | 3.7 | 4.0 | 5.6 | 4.3 | 3.1 |
| | Total | 100.0 | 100.0 | 100.0 | 100.0 | 100.0 | 100.0 |
| Test Result of Press Molding | Bending Strength (MPa) | 458 | 411 | 410 | 415 | 447 | 420 |
| | Solubility (μg/cm$^2$) | 31 | 52 | 23 | 24 | 33 | 45 |
| | Contrast Ratio | 0.98 | 0.98 | 0.95 | 0.98 | 0.97 | 0.98 |
| | Crystal System** | LDS, LP, TC | LDS, LP, TC | LDS, LP, TC | LDS, LP, TC | LDS, LP, TC | LDS, LP, TC |
| | Seizure to Investment Material | Good | Good | Good | Good | Good | Good |
| Test Result of Machining | Bending Strength (MPa) | 447 | 405 | 401 | 410 | 436 | 412 |
| | Solubility (μg/cm$^2$) | 35 | 54 | 25 | 26 | 34 | 44 |
| | Contrast Ratio | 0.96 | 0.96 | 0.95 | 0.97 | 0.94 | 0.98 |
| | Crystal System** | LDS, LMS, LP, TC | LDS, LMS, LP, TC | LDS, LMS, LP, TC | LDS, LMS, LP, TC | LDS, LMS, LP, TC | LDS, LMS, LP, TC |
| Test Result of Powder Molding | Bending Strength (MPa) | 434 | 396 | 398 | 406 | 430 | 411 |
| | Solubility (μg/cm$^2$) | 40 | 51 | 30 | 31 | 43 | 47 |
| | Contrast Ratio | 0.96 | 0.97 | 0.95 | 0.97 | 0.95 | 0.97 |
| | Crystal System** | LDS, LMS, LP, TC | LDS, LMS, LP, TC | LDS, LMS, LP, TC | LDS, LMS, LP, TC | LDS, LMS, LP, TC | LDS, LMS, LP, TC |

**LDS: lithium disilicate, LMS: lithium metasilicate, LP: lithium phosphate, TC: single crystal and/or composite crystal of a tetravalent metal oxide

TABLE 2

| | Component | Example 7 | Example 8 | Example 9 | Example 10 | Example 11 | Example 12 |
|---|---|---|---|---|---|---|---|
| Mass Ratio (%) | SiO$_2$ | 69.0 | 67.6 | 65.5 | 69.7 | 68.7 | 66.1 |
| | Li$_2$O | 16.2 | 15.5 | 14.3 | 16.0 | 14.6 | 13.6 |
| | K$_2$O | 0.5 | 5.6 | 10.0 | 6.1 | 5.7 | 6.6 |
| | P$_2$O$_5$ | 5.6 | 4.1 | 2.6 | 1.0 | 3.5 | 6.0 |
| | TiO$_2$ | 0.0 | 0.0 | 0.0 | 0.0 | 0.0 | 0.0 |
| | ZrO$_2$ | 5.4 | 2.0 | 3.5 | 4.1 | 2.0 | 4.9 |
| | SnO$_2$ | 0.0 | 0.0 | 0.0 | 0.0 | 0.0 | 0.0 |
| | CeO$_2$ | 3.3 | 5.2 | 4.1 | 3.1 | 5.5 | 2.8 |
| | Total | 100.0 | 100.0 | 100.0 | 100.0 | 100.0 | 100.0 |
| Test Result of Press Molding | Bending Strength (MPa) | 414 | 441 | 410 | 415 | 439 | 409 |
| | Solubility (μg/cm$^2$) | 21 | 33 | 48 | 51 | 35 | 47 |
| | Contrast Ratio | 0.98 | 0.98 | 0.97 | 0.98 | 0.98 | 0.98 |
| | Crystal System** | LDS, LP, TC | LDS, LP, TC | LDS, LP, TC | LDS, LP, TC | LDS, LP, TC | LDS, LP, TC |
| | Seizure to Investment Material | Good | Good | Good | Good | Good | Good |
| Test Result of Machining | Bending Strength (MPa) | 406 | 430 | 401 | 408 | 431 | 398 |
| | Solubility (μg/cm$^2$) | 27 | 46 | 52 | 55 | 42 | 56 |
| | Contrast Ratio | 0.97 | 0.98 | 0.97 | 0.97 | 0.97 | 0.98 |
| | Crystal System** | LDS, LMS, LP, TC | LDS, LMS, LP, TC | LDS, LMS, LP, TC | LDS, LMS, LP, TC | LDS, LMS, LP, TC | LDS, LMS, LP, TC |
| Test Result of Powder Molding | Bending Strength (MPa) | 391 | 422 | 394 | 390 | 425 | 390 |
| | Solubility (μg/cm$^2$) | 32 | 41 | 51 | 54 | 43 | 60 |
| | Contrast Ratio | 0.96 | 0.97 | 0.96 | 0.97 | 0.97 | 0.97 |
| | Crystal System** | LDS, LMS, LP, TC | LDS, LMS, LP, TC | LDS, LMS, LP, TC | LDS, LMS, LP, TC | LDS, LMS, LP, TC | LDS, LMS, LP, TC |

**LDS: lithium disilicate, LMS: lithium metasilicate, LP: lithium phosphate, TC: single crystal and/or composite crystal of a tetravalent metal oxide

TABLE 3

| | Component | Example 13 | Example 14 | Example 15 | Example 16 | Example 17 | Example 18 |
|---|---|---|---|---|---|---|---|
| Mass Ratio (%) | SiO$_2$ | 68.9 | 68.9 | 68.3 | 68.8 | 67.9 | 68.7 |
| | Li$_2$O | 15.1 | 15.9 | 16.0 | 14.2 | 16.1 | 15.3 |
| | K$_2$O | 4.9 | 6.7 | 5.6 | 4.1 | 4.3 | 4.5 |
| | P$_2$O$_5$ | 4.0 | 3.5 | 3.4 | 2.9 | 4.8 | 4.0 |
| | TiO$_2$ | 7.1 | 5.0 | 0.0 | 0.0 | 0.0 | 0.0 |
| | ZrO$_2$ | 0.0 | 0.0 | 6.7 | 10.0 | 0.0 | 0.0 |
| | SnO$_2$ | 0.0 | 0.0 | 0.0 | 0.0 | 6.9 | 0.0 |
| | CeO$_2$ | 0.0 | 0.0 | 0.0 | 0.0 | 0.0 | 7.7 |
| | Total | 100.0 | 100.0 | 100.0 | 100.0 | 100.0 | 100.0 |
| Test Result of Press Molding | Bending Strength (MPa) | 444 | 432 | 441 | 409 | 439 | 429 |
| | Solubility (μg/cm$^2$) | 34 | 46 | 35 | 32 | 40 | 39 |
| | Contrast Ratio | 0.98 | 0.93 | 0.97 | 0.98 | 0.98 | 0.98 |
| | Crystal System** | LDS, LP, TC | LDS, LP, TC | LDS, LP, TC | LDS, LP, TC | LDS, LP, TC | LDS, LP, TC |
| | Seizure to Investment Material | Good | Good | Good | Good | Good | Good |

TABLE 3-continued

| Component | | Example 13 | Example 14 | Example 15 | Example 16 | Example 17 | Example 18 |
|---|---|---|---|---|---|---|---|
| Test Result of Machining | Bending Strength (MPa) | 427 | 420 | 419 | 395 | 431 | 423 |
| | Solubility (μg/cm$^2$) | 43 | 51 | 46 | 40 | 42 | 45 |
| | Contrast Ratio | 0.98 | 0.92 | 0.97 | 0.97 | 0.97 | 0.98 |
| | Crystal System** | LDS, LMS, LP, TC | LDS, LMS, LP, TC | LDS, LMS, LP, TC | LDS, LMS, LP, TC | LDS, LMS, LP, TC | LDS, LMS, LP, TC |
| Test Result of Powder Molding | Bending Strength (MPa) | 415 | 413 | 409 | 389 | 404 | 412 |
| | Solubility (μg/cm$^2$) | 45 | 55 | 51 | 50 | 45 | 54 |
| | Contrast Ratio | 0.97 | 0.92 | 0.96 | 0.97 | 0.97 | 0.98 |
| | Crystal System** | LDS, LMS LP, TC | LDS, LMS LP, TC | LDS, LMS LP, TC | LDS, LMS LP, TC | LDS, LMS LP, TC | LDS, LMS LP, TC |

**LDS: lithium disilicate, LMS: lithium metasilicate, LP: lithium phosphate, TC: single crystal and/or composite crystal of a tetravalent metal oxide

TABLE 4

| Component | | Example 19 | Example 20 | Example 21 | Example 22 | Example 23 | Example 24 |
|---|---|---|---|---|---|---|---|
| Mass Ratio (%) | SiO$_2$ | 69.7 | 68.1 | 67.2 | 68.4 | 68.0 | 66.1 |
| | Li$_2$O | 15.9 | 13.8 | 14.8 | 15.7 | 13.8 | 14.2 |
| | K$_2$O | 4.9 | 5.3 | 4.2 | 6.3 | 6.6 | 5.4 |
| | P$_2$O$_5$ | 4.5 | 5.1 | 3.8 | 4.6 | 4.1 | 4.3 |
| | TiO$_2$ | 1.8 | 2.8 | 5.3 | 0.8 | 2.2 | 3.4 |
| | ZrO$_2$ | 3.2 | 4.9 | 4.7 | 0.0 | 0.0 | 0.0 |
| | SnO$_2$ | 0.0 | 0.0 | 0.0 | 4.2 | 5.3 | 6.6 |
| | CeO$_2$ | 0.0 | 0.0 | 0.0 | 0.0 | 0.0 | 0.0 |
| | Total | 100.0 | 100.0 | 100.0 | 100.0 | 100.0 | 100.0 |
| Test Result of Press Molding | Bending Strength (MPa) | 430 | 431 | 401 | 424 | 439 | 404 |
| | Solubility (μg/cm$^2$) | 29 | 36 | 35 | 32 | 38 | 42 |
| | Contrast Ratio | 0.91 | 0.97 | 0.97 | 0.89 | 0.97 | 0.98 |
| | Crystal System** | LDS, LP TC | LDS, LP TC | LDS, LP TC | LDS, LP TC | LDS, LP TC | LDS, LP TC |
| | Seizure to Investment Material | Good | Good | Good | Good | Good | Good |
| Test Result of Machining | Bending Strength (MPa) | 416 | 420 | 390 | 414 | 431 | 398 |
| | Solubility (μg/cm$^2$) | 43 | 46 | 46 | 40 | 49 | 49 |
| | Contrast Ratio | 0.91 | 0.96 | 0.97 | 0.89 | 0.98 | 0.96 |
| | Crystal System** | LDS, LMS LP, TC | LDS, LMS LP, TC | LDS, LMS LP, TC | LDS, LMS LP, TC | LDS, LMS LP, TC | LDS, LMS LP, TC |
| Test Result of Powder Molding | Bending Strength (MPa) | 402 | 406 | 391 | 411 | 416 | 394 |
| | Solubility (μg/cm$^2$) | 45 | 54 | 58 | 50 | 47 | 54 |
| | Contrast Ratio | 0.91 | 0.97 | 0.96 | 0.88 | 0.97 | 0.97 |
| | Crystal System** | LDS, LMS LP, TC | LDS, LMS LP, TC | LDS, LMS LP, TC | LDS, LMS LP, TC | LDS, LMS LP, TC | LDS, LMS LP, TC |

**LDS: lithium disilicate, LMS: lithium metasilicate, LP: lithium phosphate, TC: single crystal and/or composite crystal of a tetravalent metal oxide

TABLE 5

| | Component | Example 25 | Example 26 | Example 27 | Example 28 | Example 29 | Example 30 |
|---|---|---|---|---|---|---|---|
| Mass Ratio (%) | SiO$_2$ | 69.1 | 67.1 | 66.5 | 69.1 | 67.3 | 66.1 |
| | Li$_2$O | 15.2 | 15.3 | 14.2 | 15.6 | 14.5 | 14.2 |
| | K$_2$O | 6.1 | 5.7 | 5.4 | 5.9 | 6.0 | 5.4 |
| | P$_2$O$_5$ | 4.6 | 4.4 | 3.9 | 4.4 | 4.3 | 4.3 |
| | TiO$_2$ | 1.4 | 2.3 | 3.0 | 1.2 | 1.8 | 2.7 |
| | ZrO$_2$ | 1.2 | 1.1 | 0.8 | 0.8 | 1.1 | 1.4 |
| | SnO$_2$ | 2.4 | 4.1 | 6.2 | 2.1 | 4.2 | 4.9 |
| | CeO$_2$ | 0.0 | 0.0 | 0.0 | 0.9 | 0.8 | 1.0 |
| | Total | 100.0 | 100.0 | 100.0 | 100.0 | 100.0 | 100.0 |
| Test Result of Press Molding | Bending Strength (MPa) | 422 | 429 | 400 | 430 | 439 | 399 |
| | Solubility (μg/cm$^2$) | 46 | 31 | 35 | 41 | 48 | 38 |
| | Contrast Ratio | 0.92 | 0.97 | 0.98 | 0.90 | 0.97 | 0.98 |
| | Crystal System** | LDS, LP, TC | LDS, LP, TC | LDS, LP, TC | LDS, LP, TC | LDS, LP, TC | LDS, LP, TC |
| | Seizure to Investment Material | Good | Good | Good | Good | Good | Good |
| Test Result of Machining | Bending Strength (MPa) | 416 | 411 | 387 | 414 | 424 | 390 |
| | Solubility (μg/cm$^2$) | 56 | 46 | 40 | 52 | 53 | 49 |
| | Contrast Ratio | 0.91 | 0.97 | 0.98 | 0.91 | 0.98 | 0.96 |
| | Crystal System** | LDS, LMS, LP, TC | LDS, LMS, LP, TC | LDS, LMS, LP, TC | LDS, LMS, LP, TC | LDS, LMS, LP, TC | LDS, LMS, LP, TC |
| Test Result of Powder Molding | Bending Strength (MPa) | 405 | 401 | 381 | 408 | 416 | 381 |
| | Solubility (μg/cm$^2$) | 55 | 54 | 58 | 50 | 53 | 54 |
| | Contrast Ratio | 0.91 | 0.97 | 0.96 | 0.90 | 0.98 | 0.97 |
| | Crystal System** | LDS, LMS, LP, TC | LDS, LMS, LP, TC | LDS, LMS, LP, TC | LDS, LMS, LP, TC | LDS, LMS, LP, TC | LDS, LMS, LP, TC |

**LDS: lithium disilicate, LMS: lithium metasilicate, LP: lithium phosphate, TC: single crystal and/or composite crystal of a tetravalent metal oxide

TABLE 6

| | Component | Example 31 | Example 32 | Example 33 |
|---|---|---|---|---|
| Mass Ratio (%) | SiO$_2$ | 68.5 | 68.4 | 68.3 |
| | Li$_2$O | 15.3 | 15.3 | 15.3 |
| | K$_2$O | 4.5 | 4.5 | 4.5 |
| | P$_2$O$_5$ | 4 | 4 | 4 |
| | TiO$_2$ | 0 | 0 | 0 |
| | ZrO$_2$ | 2 | 2 | 2 |
| | SnO$_2$ | 0 | 0 | 0 |
| | CeO$_2$ | 5.5 | 5.5 | 5.5 |
| | Er$_2$O$_3$ | 0.2 | 0.2 | 0.2 |
| | V$_2$O$_5$ | 0 | 0.1 | 0.1 |
| | Ni$_2$O$_3$ | 0 | 0 | 0.1 |
| | Total | 100.0 | 100.0 | 100.0 |
| Test Result of Press Molding | Bending Strength (MPa) | 450 | 440 | 433 |
| | Solubility (μg/cm$^2$) | 35 | 32 | 40 |
| | Contrast Ratio | 0.98 | 0.98 | 0.98 |
| | Crystal System** | LDS, LMS, LP, TC | LDS, LMS, LP, TC | LDS, LMS, LP, TC |
| | Seizure to Investment Material | Good | Good | Good |
| Test Result of Machining | Bending Strength (MPa) | 450 | 428 | 432 |
| | Solubility (μg/cm$^2$) | 28 | 35 | 30 |
| | Contrast Ratio | 0.96 | 0.97 | 0.97 |
| | Crystal System** | LDS, LMS, LP, TC | LDS, LMS, LP, TC | LDS, LMS, LP, TC |
| Test Result of Powder Molding | Bending Strength (MPa) | 420 | 415 | 408 |
| | Solubility (μg/cm$^2$) | 45 | 48 | 42 |
| | Contrast Ratio | 0.98 | 0.97 | 0.97 |

TABLE 6-continued

| Component | | Example 31 | Example 32 | Example 33 |
|---|---|---|---|---|
| | Crystal System** | LDS, LMS, LP, TC | LDS, LMS, LP, TC | LDS, LMS, LP, TC |

**LDS: lithium disilicate, LMS: lithium metasilicate, LP: lithium phosphate, TC: single crystal and/or composite crystal of a tetravalent metal oxide

TABLE 7

| Component | | Comparative Example 1 | Comparative Example 2 | Comparative Example 3 | Comparative Example 4 |
|---|---|---|---|---|---|
| Mass Ratio (%) | $SiO_2$ | 66.5 | 75.0 | 65.3 | 70.4 |
| | $Li_2O$ | 10.5 | 11.7 | 13.5 | 15.6 |
| | $K_2O$ | 0.45 | 2.3 | 3.7 | 4.6 |
| | $Na_2O$ | 4.0 | — | — | — |
| | $P_2O_5$ | 3.5 | 2.2 | 5.7 | 4.1 |
| | $ZrO_2$ | 3.0 | 2.5 | — | 1.2 |
| | $Al_2O_3$ | 10.5 | 3.1 | 3.2 | — |
| | SrO | — | — | — | 0.6 |
| | ZnO | — | — | — | 0.7 |
| | $CeO_2$ | 1.5 | 1.4 | — | 2.8 |
| | $V_2O_5$ | 0.05 | — | — | — |
| | CaO | — | — | 4.1 | — |
| | F | — | — | 0.5 | — |
| | $Nb_2O_5$ | — | — | 4.0 | — |
| | Total | 100.0 | 100.0 | 100.0 | 100.0 |
| Test Result of Press Molding | Bending Strength (MPa) | 358 | 420 | 432 | 449 |
| | Solubility (μg/cm²) | 84 | 81 | 87 | 80 |
| | Contrast Ratio | 0.79 | 0.70 | 0.67 | 0.44 |
| | Crystal System** | LDS, LMS, LP, LAS | LDS, LMS, LP, C | LDS, LP, CP | LDS, LP |
| | Seizure to Investment Material | Poor | Poor | Poor | Poor |
| Test Result of Machining | Bending Strength (MPa) | 345 | 387 | 391 | 396 |
| | Solubility (μg/cm²) | 86 | 85 | 90 | 81 |
| | Contrast Ratio | 0.76 | 0.67 | 0.69 | 0.43 |
| | Crystal System** | LDS, LMS, LP, LAS | LDS, LMS, LP, C | LDS, LP, CP | LDS, LMS, LP |
| Test Result of Powder Molding | Bending Strength (MPa) | 321 | 345 | 360 | 371 |
| | Solubility (μg/cm²) | 89 | 90 | 88 | 78 |
| | Contrast Ratio | 0.73 | 0.65 | 0.65 | 0.47 |
| | Crystal System** | LDS, LMS, LP, LAS | LDS, LMS, LP, C | LDS, LP, CP | LDS, LMS, LP |

**LDS: lithium disilicate, LMS: lithium metasilicate, LP: lithium phosphate, LAS: lithium alumino silicate, C: cristobalite, CP: apatite

TABLE 8

| | 成分 | Comparative Example 5 | Comparative Example 6 | Comparative Example 7 | Comparative Example 8 | Comparative Example 9 | Comparative Example 10 |
|---|---|---|---|---|---|---|---|
| Mass Ratio (%) | $SiO_2$ | 58.4 | 80.8 | 71.2 | 65.9 | 69.7 | 68.7 |
| | $Li_2O$ | 16.8 | 11.2 | 9.1 | 19.3 | 16.2 | 12.5 |
| | $K_2O$ | 9.3 | 1.6 | 7.3 | 5.1 | 0.1 | 11.5 |
| | $P_2O_5$ | 5.6 | 1.2 | 4.2 | 3.9 | 4.8 | 2.2 |
| | $TiO_2$ | 0.0 | 0.0 | 2.3 | 1.1 | 3.4 | 1.9 |
| | $ZrO_2$ | 6.2 | 3.0 | 2.0 | 1.4 | 5.8 | 3.2 |
| | $SnO_2$ | 0.0 | 0.0 | 3.9 | 3.3 | 0.0 | 0.0 |
| | $CeO_2$ | 3.7 | 2.2 | 0.0 | 0.0 | 0.0 | 0.0 |
| | Total | 100.0 | 100.0 | 100.0 | 100.0 | 100.0 | 100.0 |
| Test Result of Press Molding | Bending Strength (MPa) | 370 | 345 | 340 | 329 | 335 | 322 |
| | Solubility (μg/cm²) | 126 | 19 | 21 | 61 | 35 | 122 |
| | Contrast Ratio | 0.95 | 0.86 | 0.90 | 0.87 | 0.92 | 0.85 |
| | Crystal System** | LDS, LMS, LP, TC | LDS, LP, TC, Q | LDS, LP, TC, Q | LDS, LMS, LP, TC | LDS, LP, TC | LDS, LP, TC |
| | Seizure to Investment Material | Poor | Poor | Poor | Poor | Poor | Poor |
| Test Result of Machining | Bending Strength (MPa) | 358 | 332 | 335 | 320 | 322 | 320 |
| | Solubility (μg/cm²) | 137 | 25 | 27 | 69 | 40 | 134 |
| | Contrast Ratio | 0.94 | 0.84 | 0.91 | 0.85 | 0.91 | 0.86 |
| | Crystal System** | LDS, LMS, LP, TC | LDS, LP, TC, Q | LDS, LP, TC, Q | LDS, LMS, LP, TC | LDS, LMS, LP, TC | LDS, LMS, LP, TC |

TABLE 8-continued

| 成分 | | Comparative Example 5 | Comparative Example 6 | Comparative Example 7 | Comparative Example 8 | Comparative Example 9 | Comparative Example 10 |
|---|---|---|---|---|---|---|---|
| Test Result of Powder Molding | Bending Strength (MPa) | 340 | 326 | 320 | 321 | 320 | 318 |
| | Solubility (μg/cm$^2$) | 140 | 26 | 30 | 70 | 45 | 143 |
| | Contrast Ratio | 0.94 | 0.84 | 0.90 | 0.84 | 0.90 | 0.85 |
| | Crystal System** | LDS, LMS, LP, TC | LDS, LP, TC, Q | LDS, LP, TC, Q | LDS, LMS, LP, TC | LDS, LMS, LP, TC | LDS, LMS, LP, TC |

**LDS: lithium disilicate, LMS: lithium metasilicate, LP: lithium phosphate, TC: single crystal and/or composite crystal of a tetravalent metal oxide, Q: quartz

TABLE 9

| | Component | Comparative Example 11 | Comparative Example 12 | Comparative Example 13 | Comparative Example 14 | Comparative Example 15 | Comparative Example 16 |
|---|---|---|---|---|---|---|---|
| Mass Ratio (%) | SiO$_2$ | 69.7 | 68.1 | 67.9 | 69.3 | 69.5 | 67.2 |
| | Li$_2$O | 15.7 | 13.5 | 14.0 | 16.3 | 16.1 | 13.8 |
| | K$_2$O | 5.6 | 4.9 | 4.1 | 5.8 | 5.2 | 4.5 |
| | P$_2$O$_5$ | 0.3 | 7.2 | 3.2 | 4.4 | 4.8 | 4.0 |
| | TiO$_2$ | 3.7 | 2.2 | 10.8 | 0.0 | 0.0 | 0.0 |
| | ZrO$_2$ | 0.0 | 0.0 | 0.0 | 4.2 | 0.0 | 0.0 |
| | SnO$_2$ | 5.0 | 4.1 | 0.0 | 0.0 | 4.4 | 0.0 |
| | CeO$_2$ | 0.0 | 0.0 | 0.0 | 0.0 | 0.0 | 10.5 |
| | Total | 100.0 | 100.0 | 100.0 | 100.0 | 100.0 | 100.0 |
| Test Result of Press Molding | Bending Strength (MPa) | 326 | 345 | 310 | 351 | 335 | 312 |
| | Solubility (μg/cm$^2$) | 56 | 119 | 55 | 49 | 39 | 41 |
| | Contrast Ratio | 0.93 | 0.90 | 0.98 | 0.78 | 0.76 | 0.97 |
| | Crystal System** | LDS, LP, TC | LDS, LP, TC | LDS, LP, TC | LDS, LP | LDS, LP | LDS, LP, TC |
| | Seizure to Investment Material | Poor | Poor | Poor | Poor | Poor | Poor |
| Test Result of Machining | Bending Strength (MPa) | 316 | 332 | 301 | 345 | 341 | 302 |
| | Solubility (μg/cm$^2$) | 63 | 125 | 60 | 55 | 49 | 50 |
| | Contrast Ratio | 0.94 | 0.91 | 0.98 | 0.76 | 0.77 | 0.95 |
| | Crystal System** | LDS, LMS, LP, TC | LDS, LP, TC | LDS, LP, TC | LDS, LMS, LP | LDS, LMS, LP | LDS, LMS, LP, TC |
| Test Result of Powder Molding | Bending Strength (MPa) | 311 | 322 | 306 | 333 | 330 | 305 |
| | Solubility (μg/cm$^2$) | 61 | 129 | 59 | 62 | 63 | 54 |
| | Contrast Ratio | 0.94 | 0.89 | 0.97 | 0.75 | 0.75 | 0.96 |
| | Crystal System** | LDS, LMS, LP, TC | LDS, LP, TC | LDS, LP, TC | LDS, LMS, LP | LDS, LMS, LP | LDS, LMS, LP, TC |

**LDS: lithium disilicate, LMS: lithium metasilicate, LP: lithium phosphate, TC: single crystal and/or composite crystal of a tetravalent metal oxide

TABLE 10

| | Component | Comparative Example 17 | Comparative Example 18 | Comparative Example 19 | Comparative Example 20 | Comparative Example 21 | Comparative Example 22 |
|---|---|---|---|---|---|---|---|
| Mass Ratio (%) | $SiO_2$ | 69.7 | 66.4 | 69.1 | 66.1 | 69.1 | 66.1 |
| | $Li_2O$ | 15.9 | 14.6 | 15.7 | 14.2 | 15.9 | 14.2 |
| | $K_2O$ | 5.9 | 4.2 | 6.3 | 4.8 | 6.1 | 5.1 |
| | $P_2O_5$ | 4.5 | 4.0 | 4.8 | 4.2 | 4.6 | 3.8 |
| | $TiO_2$ | 1.8 | 4.7 | 0.8 | 4.1 | 1.1 | 2.9 |
| | $ZrO_2$ | 2.2 | 6.1 | 0.0 | 0.0 | 0.8 | 1.8 |
| | $SnO_2$ | 0.0 | 0.0 | 3.3 | 6.6 | 2.4 | 6.1 |
| | $CeO_2$ | 0.0 | 0.0 | 0.0 | 0.0 | 0.0 | 0.0 |
| | Total | 100.0 | 100.0 | 100.0 | 100.0 | 100.0 | 100.0 |
| Test Result of Press Molding | Bending Strength (MPa) | 338 | 306 | 342 | 311 | 330 | 307 |
| | Solubility ($\mu g/cm^2$) | 43 | 51 | 47 | 47 | 59 | 39 |
| | Contrast Ratio | 0.75 | 0.97 | 0.73 | 0.98 | 0.74 | 0.97 |
| | Crystal System** | LDS, LP | LDS, LP, TC | LDS, LP | LDS, LP, TC | LDS, LP | LDS, LP, TC |
| | Seizure to Investment Material | Poor | Poor | Poor | Poor | Poor | Poor |
| Test Result of Machining | Bending Strength (MPa) | 329 | 303 | 336 | 304 | 326 | 302 |
| | Solubility ($\mu g/cm^2$) | 50 | 62 | 50 | 53 | 67 | 41 |
| | Contrast Ratio | 0.76 | 0.96 | 0.71 | 0.97 | 0.73 | 0.95 |
| | Crystal System** | LDS, LMS, LP | LDS, LP, TC | LDS, LMS, LP | LDS, LP, TC | LDS, LMS, LP | LDS, LMS, LP, TC |
| Test Result of Powder Molding | Bending Strength (MPa) | 321 | 304 | 330 | 300 | 321 | 296 |
| | Solubility ($\mu g/cm^2$) | 61 | 60 | 61 | 57 | 73 | 44 |
| | Contrast Ratio | 0.74 | 0.96 | 0.72 | 0.96 | 0.75 | 0.95 |
| | Crystal System** | LDS, LMS, LP | LDS, LP, TC | LDS, LMS, LP | LDS, LP, TC | LDS, LMS, LP | LDS, LMS, LP, TC |

**LDS: lithium disilicate, LMS: lithium metasilicate, LP: lithium phosphate, TC: single crystal and/or composite crystal of a tetravalent metal oxide

TABLE 11

| | Component | Comparative Example 23 | Comparative Example 24 |
|---|---|---|---|
| Mass Ratio (%) | $SiO_2$ | 69.5 | 65.6 |
| | $Li_2O$ | 15.9 | 14.5 |
| | $K_2O$ | 5.9 | 5.1 |
| | $P_2O_5$ | 4.6 | 4.1 |
| | $TiO_2$ | 1.2 | 2.6 |
| | $ZrO_2$ | 0.8 | 1.9 |
| | $SnO_2$ | 1.2 | 4.9 |
| | $CeO_2$ | 0.9 | 1.3 |
| | Total | 100.0 | 100.0 |
| Test Result of Press Molding | Bending Strength (MPa) | 335 | 309 |
| | Solubility ($\mu g/cm^2$) | 40 | 42 |
| | Contrast Ratio | 0.73 | 0.97 |
| | Crystal System** | LDS, LP | LDS, LP, TC |
| | Seizure to Investment Material | Poor | Poor |
| Test Result of Machining | Bending Strength (MPa) | 322 | 302 |
| | Solubility ($\mu g/cm^2$) | 47 | 51 |
| | Contrast Ratio | 0.72 | 0.96 |
| | Crystal System** | LDS, LMS, LP | LDS, LP, TC |
| Test Result of Powder Molding | Bending Strength (MPa) | 315 | 299 |
| | Solubility ($\mu g/cm^2$) | 52 | 58 |
| | Contrast Ratio | 0.73 | 0.97 |
| | Crystal System** | LDS, LMS, LP | LDS, LP, TC |

**LDS: lithium disilicate, LMS: lithium metasilicate, LP: lithium phosphate, TC: single crystal and/or composite crystal of a tetravalent metal oxide In the all examples, the contrast ratio was within a range of 0.88 to 0.99 and high shielding property was exhibited. In addition, the bending strength is 380 MPa or more in press molding, and high material strength was exhibited.

On the other hand, in the Comparative examples 1 to 4, the contrast ratio was low (less than 0.80), and sufficient shielding property was not exhibited. In the Comparative examples 5 to 24, the bending strength was less than 350 MPa in at least one of the Press Molding, the Machining and Powder Molding, and sufficient material strength was not exhibited.

As for the solubility, the solubility of all Examples were within the standard value (100 μg/cm$^2$) of ISO6872, and a high chemical durability (low solubility) was exhibited in every Example.

On the hand, the solubility of some Comparative examples were not within the standard value (100 μg/cm$^2$) of ISO6872. Further, although the solubility was within the standard value (100 μg/cm$^2$) of ISO6872 in the Comparative examples, the bending strength was less than 350 MPa in at least one of the Press Molding, the Machining and Powder Molding, and sufficient material strength was not exhibited.

Examples were free from the seizure to the investment material to give satisfactory results. On the other hand, in Comparative Examples, the seizure to the investment material was observed on the specimen surface in many cases.

From the above-described results, each of the dental lithium silicate glass ceramics exhibited satisfactory results such as a high shielding property and a high material strength which were not achieved in the conventional dental lithium silicate glass ceramics. The dental lithium silicate glass composition of the present invention exhibited a high chemical durability. This is probably due to the fact that by heat treating the dental lithium silicate glass composition of the present invention, having specific content ranges of oxides, the main crystal (lithium disilicate and/or lithium metasilicate) and the secondary crystal (single crystal and/or composite crystal of a tetravalent metal oxide) were precipitated efficiently and in a high density. Specifically, the shielding property was improved by increasing the refractive index caused by containing the secondary crystal (single crystal and/or composite crystal of a tetravalent metal oxide).

Consequently, the dental lithium silicate glass composition of the present invention drastically improves the shielding property as compared with conventional lithium silicate glass compositions containing the main crystal (lithium disilicate and/or lithium metasilicate).

With respect to the use of substantially any plural and/or singular terms herein, those having skill in the art can translate from the plural to the singular and/or from the singular to the plural as is appropriate to the context.

Although the description herein has been given with reference to the drawings and embodiments, it should be noted that those skilled in the art may make various changes and modifications on the basis of this disclosure without difficulty. Accordingly, any such changes and modifications are intended to be included in the scope of the embodiments.

INDUSTRIAL APPLICABILITY

The dental lithium silicate glass composition provided by the present invention has a high shielding property, a high material strength and a high chemical stability (high chemical durability, low reactivity) allowing the ceramic concerned to be applied to a blank for press molding, a blank for machining and a powder porcelain, and is capable of being applied to various dental crown restorative materials in the restorative treatment of the dental field.

BRIEF DESCRIPTION OF DRAWINGS

FIG. 1 is a graph showing the TG-DTA curve in Example 1;

FIG. 2 shows the XRD pattern after the first crystallization in Example 1;

FIG. 3 shows the XRD pattern after the second crystallization in Example 1;

FIG. 4 shows the SEM image after the first crystallization in Example 1; and

FIG. 5 is the SEM image after the second crystallization in Example 1.

What is claimed is:

1. An $Al_2O_3$-free dental lithium silicate glass composition consisting of the following components:
   $SiO_2$: 60.0 to 80.0% by weight,
   $Li_2O$: 10.0 to 17.0% by weight,
   $K_2O$: 0.5 to 10.0% by weight,
   a nucleating agent: 1.0 to 6.0% by weight,
   a colorant: 0.0 to 10.0% by weight, and,
   a metal oxide Me(tetravalent)$O_2$: 5.0 to 10.0% by weight,
   wherein
      the nucleating agent is at least one selected from a group consisting of $P_2O_5$, $WO_3$, $V_2O_5$, Pt and Ag,
      the colorant is at least one selected from a group consisting of MnO, $Fe_2O_3$, $Tb_4O_7$, $Eu_2O_3$, $Ni_2O_3$, $Cr_2O_3$, $Co_2O_3$, $Nd_2O_3$, $Pr_6O_{11}$, $Sm_2O_3$, $V_2O_5$, $Dy_2O_3$, $Ho_2O_3$ and $Er_2O_3$, and
      the metal oxide Me(tetravalent)$O_2$ is at least one selected from a group consisting of $TiO_2$, $ZrO_2$, $SnO_2$, $HfO_2$, $PbO_2$ and $CeO_2$.

2. A dental lithium silicate glass ceramic comprising a heat treated product of the glass composition according to claim 1, wherein the precipitate of a lithium metasilicate crystal and/or a lithium disilicate crystal is included as a main crystal phase, and the precipitate of a single crystal and/or a composite crystal of a tetravalent metal oxide is included as a secondary crystal phase.

3. A dental crown restorative material prepared by thermocompression molding, mechanical processing and building up/firing of a glass ceramic obtained by heat treating the glass composition according to claim 1.

4. A dental crown restorative material prepared by thermocompression molding, mechanical processing and building up/firing of the glass ceramic according to claim 2.

* * * * *